(12) United States Patent
DeCoste et al.

(10) Patent No.: US 10,272,639 B2
(45) Date of Patent: Apr. 30, 2019

(54) ABRASION RESISTANT FILM FOR BIOCONTAINERS

(71) Applicant: EMD Millipore Corporation, Burlington, MA (US)

(72) Inventors: David DeCoste, Chelmsford, MA (US); Joseph Cianciolo, Hudson, NH (US); Michael Furbush, Dracut, MA (US); John Saragosa, Melrose, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 15/544,644

(22) PCT Filed: Mar. 22, 2016

(86) PCT No.: PCT/US2016/023534
§ 371 (c)(1),
(2) Date: Jul. 19, 2017

(87) PCT Pub. No.: WO2016/154180
PCT Pub. Date: Sep. 29, 2016

(65) Prior Publication Data
US 2017/0368790 A1 Dec. 28, 2017

Related U.S. Application Data

(60) Provisional application No. 62/136,691, filed on Mar. 23, 2015.

(51) Int. Cl.
*B32B 5/02* (2006.01)
*B32B 27/08* (2006.01)
(Continued)

(52) U.S. Cl.
CPC .............. *B32B 5/024* (2013.01); *B01L 3/508* (2013.01); *B32B 5/02* (2013.01); *B32B 5/022* (2013.01);
(Continued)

(58) Field of Classification Search
CPC ...................................... B32B 27/12
(Continued)

(56) References Cited

U.S. PATENT DOCUMENTS 3,169,899 A 2/1965 Steuber
3,276,944 A 10/1966 Levy
(Continued)

FOREIGN PATENT DOCUMENTS

CA 1055641 A 5/1979
DE 10301984 A1 7/2004
(Continued)

OTHER PUBLICATIONS

International Search Report and Written Opinion received for PCT Patent Application No. PCT/US2016/023534, dated Jun. 3, 2016, 10 pages.
(Continued)

*Primary Examiner* — Donnell A Long
(74) *Attorney, Agent, or Firm* — EMD Millipore Corporation

(57) ABSTRACT

A biocontainer film enhanced with an abrasion resistant or "cut-proof" substrate. Such substrates can be combined with current biocontainer materials, via various techniques of embedding, coextrusion or laminating, to maintain the cleanliness and low extractables already validated for biotech manufacturing. The substrate of choice may be constructed from materials known to be more resistant to abrasion and sharp razor type cuts or from materials oriented in such a way to prevent puncture to occur. The new (Continued)

substrate must also be flexible to allow for typical folding as demonstrated by current packaging practices. The new substrate may be constructed from materials other than polymers such as metal, glass or carbon or in combination with polymers. A non-constrained pressure test is also disclosed.

19 Claims, 11 Drawing Sheets

(51) Int. Cl.
    *B32B 27/12* (2006.01)
    *B32B 27/32* (2006.01)
    *B32B 27/34* (2006.01)
    *B32B 27/40* (2006.01)
    *B01L 3/00* (2006.01)
    *B65D 65/40* (2006.01)
    *B65D 75/58* (2006.01)
    *G01M 3/32* (2006.01)

(52) U.S. Cl.
    CPC .............. *B32B 27/08* (2013.01); *B32B 27/12* (2013.01); *B32B 27/32* (2013.01); *B32B 27/34* (2013.01); *B32B 27/40* (2013.01); *B65D 65/40* (2013.01); *B65D 75/58* (2013.01); *G01M 3/3272* (2013.01); *B01L 2300/0887* (2013.01); *B01L 2300/16* (2013.01); *B32B 2262/0253* (2013.01); *B32B 2262/0261* (2013.01); *B32B 2262/0269* (2013.01); *B32B 2262/0276* (2013.01); *B32B 2262/103* (2013.01); *B32B 2262/106* (2013.01); *B32B 2307/554* (2013.01); *B32B 2307/7242* (2013.01); *B32B 2439/40* (2013.01); *B32B 2439/80* (2013.01); *B65D 2275/00* (2013.01)

(58) Field of Classification Search
    USPC .......... 222/92, 105, 399, 396, 397, 478, 481, 222/156, 157
    See application file for complete search history.

(56) References Cited

U.S. PATENT DOCUMENTS

| | | | |
|---|---|---|---|
| 3,388,201 | A | 6/1968 | Mazzolini et al. |
| 4,326,574 | A | 4/1982 | Pallaroni et al. |
| 4,812,359 | A | 3/1989 | Hall |
| 5,173,345 | A | 12/1992 | Dehennau et al. |
| 5,180,614 | A | 1/1993 | Escabasse |
| 5,199,609 | A * | 4/1993 | Ash, Jr. ................ B67D 1/0406 141/114 |
| 5,568,657 | A | 10/1996 | Cordova et al. |
| 5,860,566 | A * | 1/1999 | Lucs ....................... A01C 7/02 222/1 |
| 6,045,648 | A | 4/2000 | Palmgren et al. |
| 6,235,825 | B1 | 5/2001 | Yoshida et al. |
| 6,957,523 | B2 | 10/2005 | Siccardi |
| 8,053,048 | B2 | 11/2011 | Lang et al. |
| 2005/0196630 | A1 | 9/2005 | Carper et al. |
| 2009/0130355 | A1 | 5/2009 | Chen et al. |
| 2011/0274901 | A1 | 11/2011 | Ronzani |
| 2012/0219609 | A1 | 8/2012 | Howland |
| 2014/0083170 | A1 * | 3/2014 | Pavlik ................. G01M 3/3263 73/49.2 |
| 2015/0298438 | A1 * | 10/2015 | Nevalainen ............. B32B 27/08 206/524.6 |
| 2016/0177048 | A1 * | 6/2016 | Topolkaraev ........... C08L 67/04 521/134 |
| 2018/0099495 | A1 * | 4/2018 | Bruce ................. A61F 13/4902 |
| 2018/0272019 | A1 * | 9/2018 | Roberts ..................... A61L 2/20 |

FOREIGN PATENT DOCUMENTS

| | | |
|---|---|---|
| DE | 102010019837 A1 | 11/2011 |
| EP | 0157646 A2 | 10/1985 |
| EP | 0114964 B1 | 11/1986 |
| EP | 0229475 A1 | 7/1987 |
| EP | 0232171 A2 | 8/1987 |
| EP | 0259899 A1 | 3/1988 |
| EP | 0468579 A1 | 1/1992 |
| EP | 0658421 A1 | 6/1995 |
| EP | 0698044 A1 | 2/1996 |
| EP | 0713445 A1 | 5/1996 |
| EP | 0625951 B1 | 3/1997 |
| EP | 0506807 B1 | 5/1998 |
| EP | 0877051 A1 | 11/1998 |
| EP | 1391288 A1 | 2/2004 |
| EP | 0980894 B1 | 6/2004 |
| EP | 1007414 B1 | 6/2005 |
| EP | 1587607 A2 | 10/2005 |
| EP | 1698523 A2 | 9/2006 |
| EP | 1682349 B1 | 4/2008 |
| EP | 2077096 A1 | 7/2009 |
| EP | 1796571 B1 | 10/2009 |
| EP | 1877484 B1 | 6/2011 |
| EP | 2344332 B1 | 7/2012 |
| EP | 2501247 A4 | 1/2017 |
| FR | 1485789 A | 6/1967 |
| GB | 970070 A | 9/1964 |
| GB | 991496 A | 5/1965 |
| GB | 1067577 A | 5/1967 |
| GB | 1580128 A | 11/1980 |
| JP | 4-074646 A | 3/1992 |
| JP | 10-237738 A | 9/1998 |
| JP | 10-237741 A | 9/1998 |
| JP | 11-198264 A | 7/1999 |
| JP | 2002-240220 A | 8/2002 |
| JP | 2003-145608 A | 5/2003 |
| JP | 2005-206808 A | 8/2005 |
| JP | 2007-246148 A | 9/2007 |
| JP | 2010-264137 A | 11/2010 |
| WO | 1994/13559 A1 | 6/1994 |
| WO | 1994/26793 A1 | 11/1994 |
| WO | 1995/04655 A2 | 2/1995 |
| WO | 1995/16565 A1 | 6/1995 |
| WO | 2004/064478 A2 | 8/2004 |
| WO | 2008/040567 A1 | 4/2008 |
| WO | 2008/150951 A1 | 12/2008 |
| WO | 2009/151225 A3 | 12/2009 |
| WO | 2011/063261 A2 | 5/2011 |
| WO | 2012/151223 A1 | 11/2012 |
| WO | 2012/166523 A1 | 12/2012 |
| WO | 2013/022670 A1 | 2/2013 |
| WO | 2014/083466 A1 | 6/2014 |

OTHER PUBLICATIONS

International Preliminary Report on Patentability and Written Opinion received for PCT Application No. PCT/US2016/023534, dated Sep. 26, 2017, 7 pages.

* cited by examiner

ABRASION RESISTANT FILM FOR BIOCONTAINERS

RELATED APPLICATIONS

The present application is a US National Stage application of International Application No. PCT/US2016/023534, filed Mar. 22, 2016, which claims the benefit of priority of U.S. Provisional Patent Application No. 62/136,691, filed Mar. 23, 2015, each of which is incorporated by reference herein in its entirety.

The present invention relates to abrasion resistant films. More particularly it relates to abrasion resistant films for biocontainers.

BACKGROUND OF THE INVENTION

The use of single use bags and other biocontainers is growing in the pharmaceutical and biopharmaceutical business. These bags replace stainless tanks, totes and bins for the processing and transportation of liquids and solids such as raw materials, intermediates and finished goods.

Such film are typically multilayered plastic film structures. They are typically laminates of 4 or more layers (generally between 4 and 10 layers). They generally have 3 or more zones or layers, an inner contact zone which is in contact with the liquid within the bag and which is one or more layers of a generally inert material such as polyethylene that is not likely to release extractables, such as oils or fillers into the content of the bag; an intermediate zone, which often has one or more gas impermeable layers such as ethylene vinyl acetate (EVA), polyethylene vinyl alcohol (EVOH), and the like; and an outer strength zone which provides support, burst resistance and some measure of protection to the remaining zones of the biocontainer and which is generally formed of one or more layers of plastics such as polyethylene, polypropylene, polyethylene-vinyl acetate (EVA), polyethylene teraphthalate (PET), polyamide (nylon), and the like.

Biocontainers are generally inspected and gross leak tested for defects before they are shipped to the user, however, current films in biocontainers lack the strength, toughness and durability to survive the multiple manipulation steps used in atypical biotech facility to unpackage, install and use such a biocontainer. Due mostly to operator handling there is still the chance for a cut, puncture or abrasion to occur to the biocontainer. This can lead to not only loss of the biocontainer but also of its contents which in the case of pharmaceuticals especially biopharmaceuticals represents a significant monetary loss.

What is needed is a new biocontainer and film for biocontainers which is resistant to cuts, punctures and abrasions.

SUMMARY OF THE INVENTION

A biocontainer film enhanced with an abrasion and cut resistant substrate. Such substrates can be combined with current existing biocontainer films, by various techniques such as embedding, coextrusion and lamination either in the intermediate zone or the outer zone to maintain the cleanliness and low extractables of the inner zone that has already been validated for biotech manufacturing. The substrate of choice is constructed of materials known to be more resistant to abrasion and cuts or materials that are oriented in a way to prevent puncturing from occurring. It may be formed of polymers or other materials such as polymer, glass, metal, or carbon fibers alone or in combination with polymers. The new substrate is flexible so as to allow for the typical folding of the biocontainer and may also be in the form of a web. The substrate maybe a woven or nonwoven material. The substrate generally has an attachment or binding layer by which the substrate can be attached to the internal or outer surface of the film. Openings can be formed in the substrate to provide a visual opening or window into the interior of the container made by the film or a port. The biocontainer has a selectively closed inner volume that can contain one or more fluids and/or solids. Preferably, the inner volume contains one or more gases and one or more fluids.

It is an object of the present invention to provide a material for biocontainers comprising a film formed of one or more layers, the film having an interior and exterior side, and a substrate attached to the exterior side of the film wherein the substrate is formed of a fibrous material so as to provide abrasion resistance to the material.

It is a further object of the present invention to provide a material formed of a film and a substrate attached to it wherein the substrate is formed with a polymer backing to attach the substrate to the film.

It is an additional object of the present invention to provide a material formed of a film and a substrate attached to it wherein the substrate is formed with a polymer backing to attach the substrate to the film, the substrate is formed of a material selected from the group consisting of woven and non-woven fibrous material and the polymer backing of the substrate is selected from the group consisting of polyolefins, polyurethanes and nylons.

It is an additional object of the present invention to provide a material formed of a film and a substrate attached to it wherein the substrate is formed of a material selected from the group consisting of woven fibrous material selected from the group consisting of a material selected from the group consisting of polymers, metal fibers, glass fibers, and carbon fibers.

It is an additional object of the present invention to provide a material formed of a film and a substrate attached to it wherein the substrate is formed of a material selected from the group consisting of woven fibrous material selected from the group consisting of nylon, polyester, aramids and polyolefins.

It is another object of the present invention to provide a material formed of a film and a substrate attached to it wherein the substrate is formed of a non-woven fibrous material selected from the group consisting of a material selected from the group consisting of polymers, metal fibers and glass fibers.

It is another object of the present invention to provide a material formed of a film and a substrate attached to it wherein the substrate is formed of a non-woven fibrous polymeric material selected from the group consisting of nylons, polyesters, aramids and polyolefins.

It is a further object of the present invention to provide a material formed of a film and a substrate attached to it wherein the film is formed of a multilayered film having a first interior side layer formed of one or more layers forming an inner contact zone, one or more layers of a gas impermeable zone and one or more layers of polymers on the exterior side of the of gas impermeable zone forming an outer strength zone.

It is another object of the present invention to provide a material formed of a film and a substrate attached to it wherein the substrate has one or more openings to form a window or a port opening.

It is an additional object of the present invention to provide a material formed of a film and a substrate attached to it wherein the substrate has one or more elongate openings to form a window.

It is an object of the present invention to provide a material for biocontainers comprising a film formed of one or more layers, the film having an interior and exterior side, and a substrate attached to the exterior side of the film wherein the substrate is formed of a fibrous material so as to provide abrasion resistance to the material and the fibrous material is enveloped or encapsulated in an outer protective layer to increase abrasion resistance and decrease pilling.

It is a further object of the present invention to provide a biocontainer formed of any, all, or selected combinations of the objects above.

It is another object of the present invention to provide a biocontainer formed of any, all, or selected combinations of the objects above which is capable of being pressure tested without the need of constraints or use of low pressures.

It is a further object of the present invention to provide a biocontainer formed of any, all, or selected combinations of the objects above which is capable of dispensing or moving fluid (gas and/or liquid) through the biocontainer by the use of gas pressure contained within the biocontainer (either statically or continually).

These and other objects will become clear from the description, claims, and drawings below.

IN THE DRAWINGS

DETAILED DESCRIPTION OF THE INVENTION

Figure 1A:
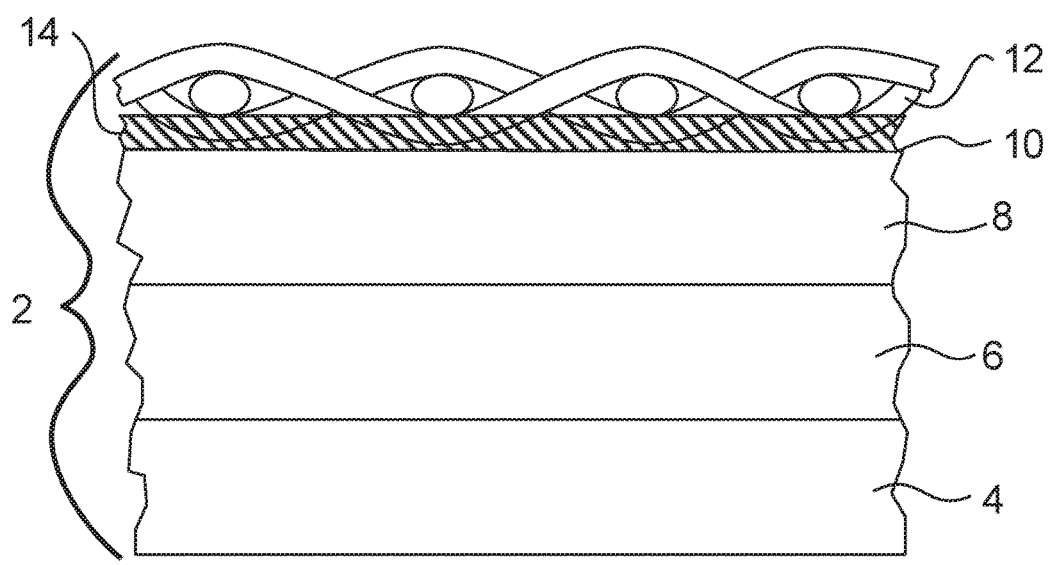
FIG. 1A shows a cross section of a first embodiment of the present invention and FIG. 1B shows a cross section of a second embodiment of the present invention.

FIG. 1 shows a cross section of an enhanced biocontainer film according to the present invention.

The film 2 has an inner contact zone 4 which is in contact with the liquid within a biocontainer that formed from the film. The inner contact zone may be formed of one or more layers of material that are inert to the liquids that may be in contact with the film and which is/are also low in extractables that might enter the liquid in contact with the inner contact zone 4 of the film 2. Such materials include but are not limited to various polyolefins such as polyethylene.

Outward of this inner contact zone 4 is an intermediate zone which typically is a gas impermeable zone 6 formed of one or more layers of materials that are gas impermeable. Such materials include but are not limited to polymers such as ethylene vinyl acetates (EVA) and ethylene vinyl alcohols (EVOH) and various metal foils such as aluminum.

Outward of this gas impermeable zone 6 is an outer strength zone 8 formed of one or more layers which provides support, burst resistance and some measure of protection to the remaining zones of the film 2. Such materials include but are not limited to various grades of polyethylene such as high density polyethylene, polypropylene, nylons, polyethylene teraphthalate (PET), EVA, polyamide and the like.

Attached to the outer surface 10 of the outer strength zone 8 is the substrate 12.

In this instance, each of the zones 4, 6, 8 are represented by one layer but as mentioned above each zone may be formed of one or more layers bound together to form a film 2.

Such films 2 are well known and commercially available such as Pureflex™ film available from EMD Millipore Corporation, Billerica, Mass., HYQC-5X-14 film from Thermofisher Inc, Waltham Mass. and FlexSafe or S71 or S40 available from Sartorius Stedim Biotech GmbH of Goettingen Germany.

The substrate 12 as shown is a woven material, although as mentioned above it can equally be a nonwoven or spunbonded material or it may be a netting material such as Delnet film, which is an aperture or porous stretched film.

The substrate can be formed of polymer fibers or yarns, metal fibers or yarns or glass fibers or yarns.

Polymer substrates generally woven, nonwoven or netted can be formed of polymeric materials such as nylons, KEVLAR® and other amides, PET, EVA, polyethylenes, polypropylenes and the like.

Polymeric woven fabrics can be any such fabric. They are commercially available either as a fabric alone or a coated fabric which has a tie resin layer 14 (see below) already integrated into it. Such materials are available from a variety of companies such as Eastex Products Inc. of Holbrook, Mass.; PGI Inc. of Charlotte, N.C.; or Freudenberg & Co KG of Manchester, N.H.

Nonwovens can be for example spunbonded or blown materials and are commercially available for instance as Typar® or Tyvek® sheets from EI DuPont De Nemours of Wilmington, Del.

Metal substrates, generally available as woven or nonwoven, can be formed of stainless steel, aluminum and the like. Preferably a noncorrosive metal or a metal treated with a noncorrosive outer layer such as epoxy or nickel are preferred. These are typically provided as a woven cloth or a screen material.

Glass substrates are generally woven or nonwoven. Fiberglass cloths and fiberglass mats are preferred.

Carbon fiber substrates can also be found commercially in woven, web forms such as Panex® 30 or 35 carbon fiber webs from Zoltek Corporation, St Louis, Mo.

The substrate 12 can be attached to the outer zone 8 by an attachment or tie resin layer 14 (see FIG. 1A) such as a thermoplastic material which preferably is at least partially embedded into the substrate 12 as shown. It may be provided with the substrate 12 or added to the substrate 12 before use. Alternatively, it 14 can be formed as part of the film making process as an additional layer especially when a lamination process is used. In some instances, the substrate 12 does not need a tie resin layer 14 if the substrate 12 is incorporated into the film 2 as a heat bonded material or is integrated as part of the film manufacturing process as shown in FIG. 1B.

Figure 2A:
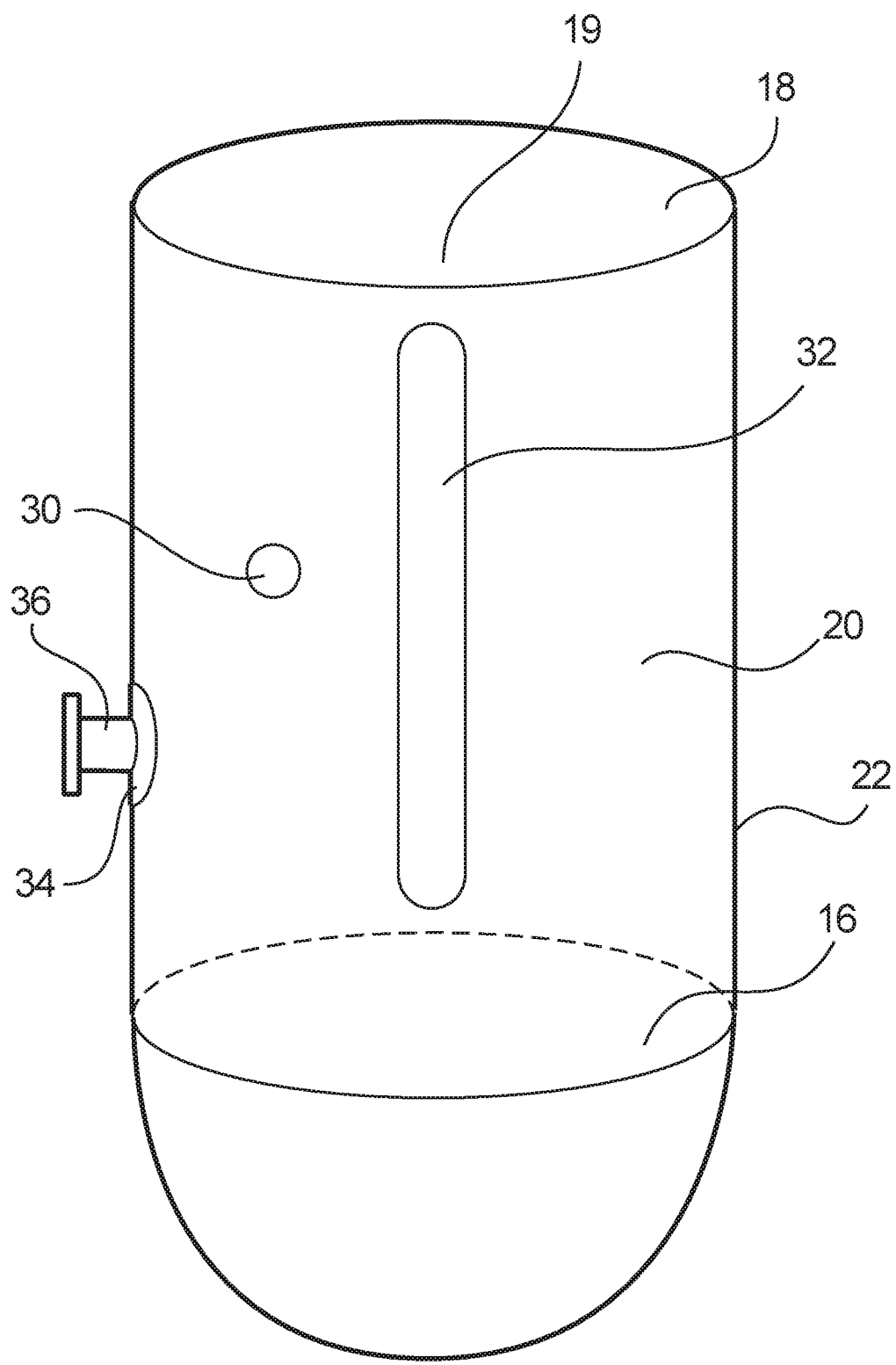
FIG. 2A shows a biocontainer formed in accordance with the present invention in cross sectional view.

In FIG. 2A, the biocontainer 22 is shown in its filled configuration. It typically is filled with at least some liquid and some gas such as air near the top although for testing it may be filled with air or selected gases only. The biocontainer 22 is known as a 3D type of bag.

This film 2 is cut to shape into one or several pieces which form the bottom 16, top 18 and side(s) 20 of the biocontainer 22 as shown in FIG. 2. The biocontainer has an inner volume 19 formed by the bottom 16, top 18 and side(s) 20 of the biocontainer 22 which can be used to hold various fluids (gases, liquids, both) and/or solids.

Also shown in FIG. 2A are windows or viewing ports 30, 32 which are formed by making an opening in the substrate 12 before it is attached to the film 2. As shown at window 30 the opening is circular. As shown in window 32 it is elongate so as to allow one to view essentially the entire height of the filled biocontainer. As shown in window 30, one may form a rim 34 around the opening such as by impregnating the cut edge and adjacent substrate with a polymer or attaching a polymeric disk with an open center sized to mate with the desired port size to the substrate 12 to reduce or eliminate any potential for the substrate fiber(s) to become loose. Alternatively, when using a tie layer 14, that layer 14 itself often provides sufficient attachment to the fiber(s) of the substrate 12 to prevent this from occurring.

Additionally, one can form port openings in the substrate 12 and film 2 as shown at port opening 34. One can simply cut the opening 34 with a die, punch or knife, whether heated or unheated or a laser, as desired, to the finished material before it is formed into a biocontainer. Other methods of cutting also be used. If desired, one may first cut the substrate 12 before its attachment to the film 2 and then use it as a guide to cut the film 2 beneath it to form the opening 34.

Alternatively, if one uses a transparent or translucent material for the substrate 12, such as nylon, polyethylene or polypropylene, one can simply form a window 30, 32 by heat melting the substrate 12 in the desired area to form the window 30, 32 before the substrate 12 is attached to the film 2. A first means for doing so is to use an iron or heated platen to heat melt the substrate 12 in the desired area with pressure as well as to cause the substrate to form the desired window. Alternatively, a RF heater or an impulse welder could be used to heat and melt the substrate 12. The window 30 can be formed in the substrate 12 before it is attached to the film 2. Alternatively, when the window 30 is formed in the substrate 12 after its attachment to the film 2, the substrate 12 is of a material having a melting point lower than that of the film 2 and it is only heated to the temperature below that of the melting point of the film 2.

Figure 2B:
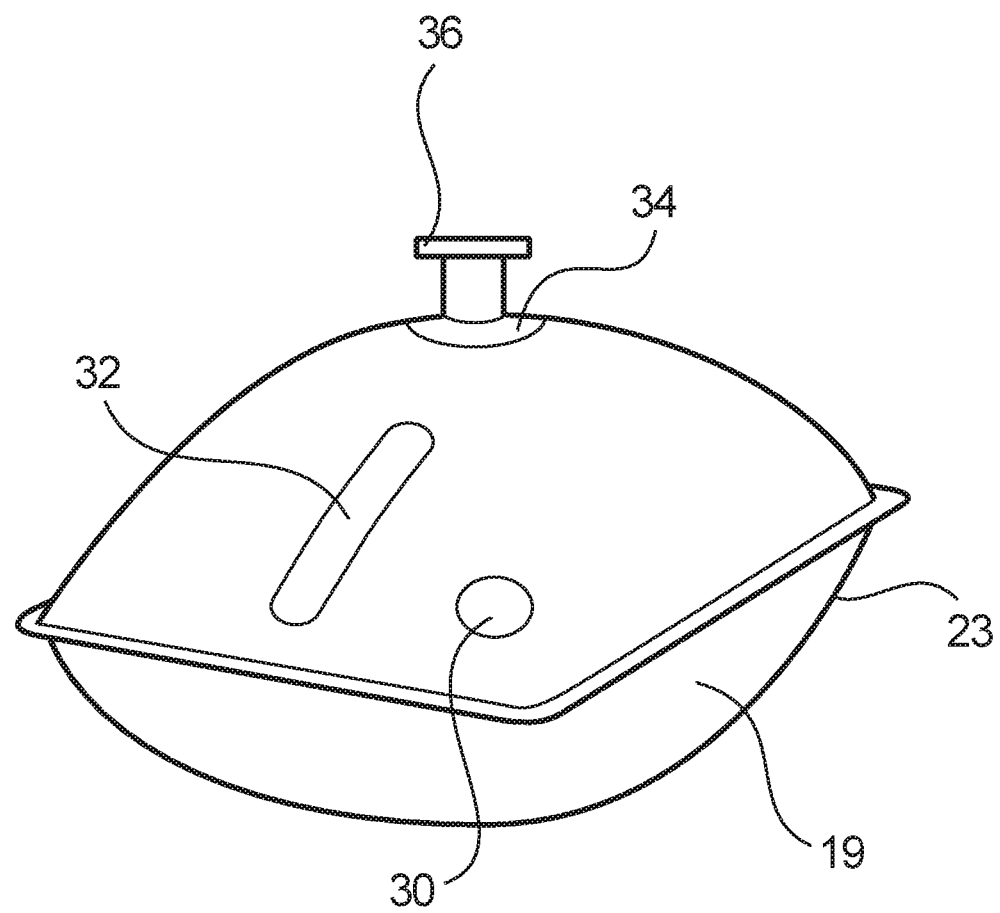
FIG. 2B shows another biocontainer formed in accordance with the present invention in planar view.

FIG. 2B shows what is known as a 2D or pillow type biocontainer 23. Is formed generally of one or two pieces of film. The film (if one piece) is folded on itself and sealed along its outer edges to form the biocontainer 23. Alternatively, it is formed of two pieces of film that are sealed together along their outer edges. In either configuration, an inner volume 19 is formed that is selectively sealed off from the environment. As in FIG. 2A the use of windows 30, 32, port openings 34 and fittings 36 can be used and assembled in the same manner as in FIG. 2A.

Figure 3:
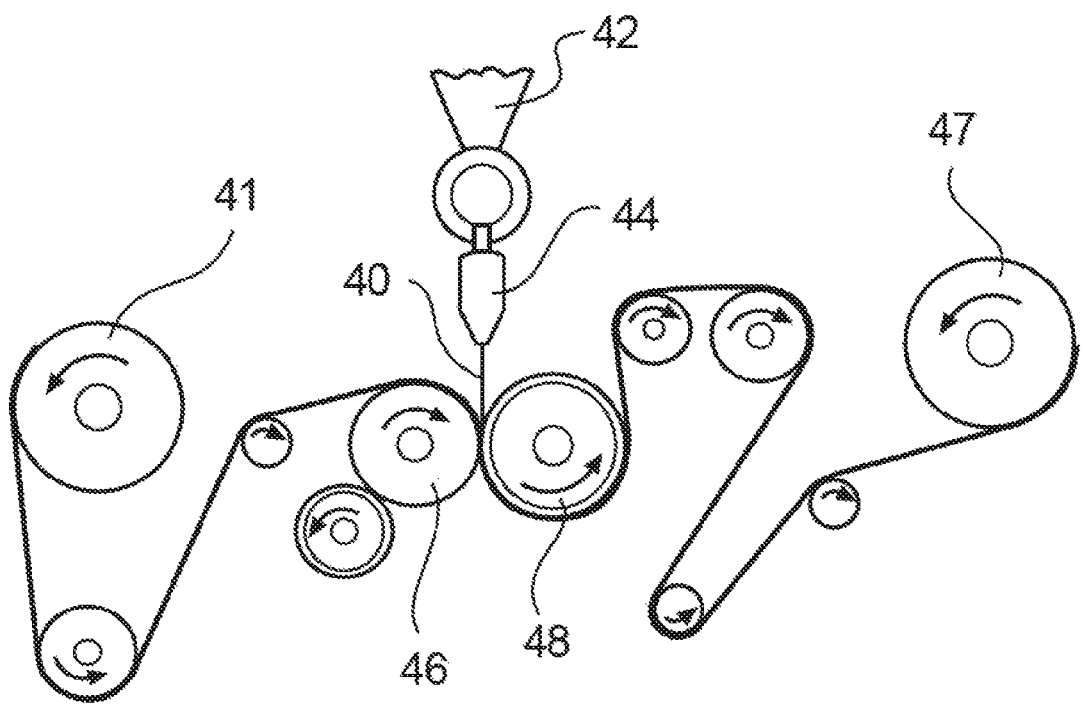
FIG. 3 shows a method of forming the material according to the present invention in planar view.
Figure 4:
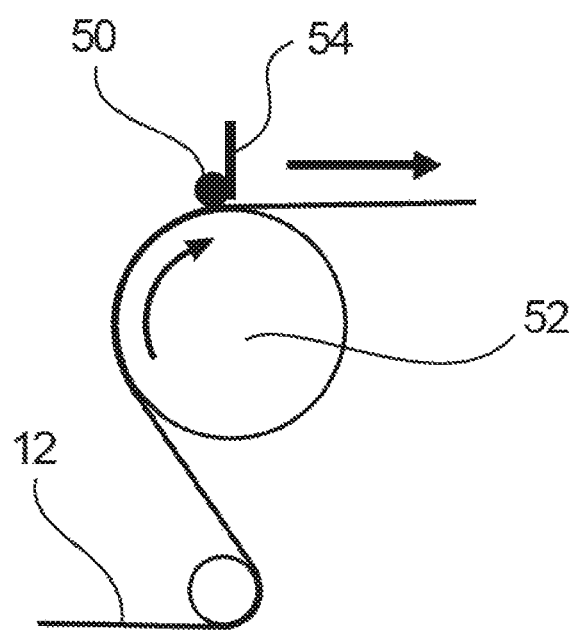
FIG. 4 shows another method of forming the material according to the present invention in planar view.

FIGS. 3 and 4 illustrate typical methods for applying a polymer attachment layer or tie resin layer 40, 50 to the substrates 12 to be used in this application. The substrate 12 with the tie resin layer 40, 50 is then attached to the underlying film 2 by a variety of methods including but not limited to heat lamination, adhesive or chemical bonding and the like.

FIG. 3 shows an extrusion coating method that melts the polymer resin layer 40 of choice via an extruder 42 and applying it through a die 44 while still in the melt phase onto the chosen substrate 12. The substrate 12 is typically of a higher melting point material to avoid dimensional changes upon contact with the molten resin 40. It is unwound from an unwind roll 41. A pressure 46 and chill roll 48 mechanism is employed to ensure that the two mating materials 12, 40 are combined with good adhesion into one, new, multilayered substrate 12. The finished product is taken up on a windup roll 47.

FIG. 4 is an alternate method used for very thin polymer coatings 50 which is usually a mixture of polymer and volatile solvent for the polymer, the solvent is vaporized downstream via a series of ovens. The substrate 12 is moved over a coating drum 52 while the coating compound 50 is applied such as by a coating knife 54. The result is a well adhered, multilayer structure.

An additional method (not shown) for combining multilayered structures is via a hot press laminator. In this process, two different structures such as a substrate 12 and a film 2 are heated and pressed together until cool. This equipment is typically comprised of a series of heating and cooling rolls.

Another method of combining multilayered structures is to apply a layer of hot melt thermoplastic to either the substrate surface that will be adjacent the film or to the film that will be adjacent the substrate and then press them into contact with each other to form a good bond. The biocontainer can be a 2-dimensional biocontainer or a 3-dimensional biocontainer (such as is shown in FIG. 2). The biocontainer has an inner volume defined by its sealed sides, top and bottom. The volume can range from 1 liter to 2000 liters. Typically. There are a variety of sizes made available such as 1, 5, 10, 20, 50, 100, 200, 500, 1000 and 2000 liters although custom volumes may also be made as desired. The biocontainer may be open to the environment, For example, the top may be open or it can be selectively closed from the environment with various ports and inlets or outlets providing selective access to the inner volume of the biocontainer. It can used to store or process fluids, (gases, liquids or combinations of both) and/or solids and may be formed into a bioreactor or mixer or storage bag. For example, the biocontainer may be a mixer and may be used to mix various liquids together or a liquid or liquids with one or more solids such as buffer media, cell culture media and the like. It may also be a bioreactor or fermentor used to grow animal cells such as mammalian or insect cells including CHO (Chinese Hamster Ovary cells); bacteria such as *E. coli*; yeasts; fungi; and the like. It may be used for the storage or transport of liquids such as intermediate or finished pharmaceutical products. They are of particular value in pharmaceutical and biopharmaceutical, veterinary, nutriceutical, stem cell manufacturing, ADC manufacturing and vaccine production. Various additions such as impellers, sensors, gas and liquid tube sets and the like may also be added as desired.

Figure 1B:
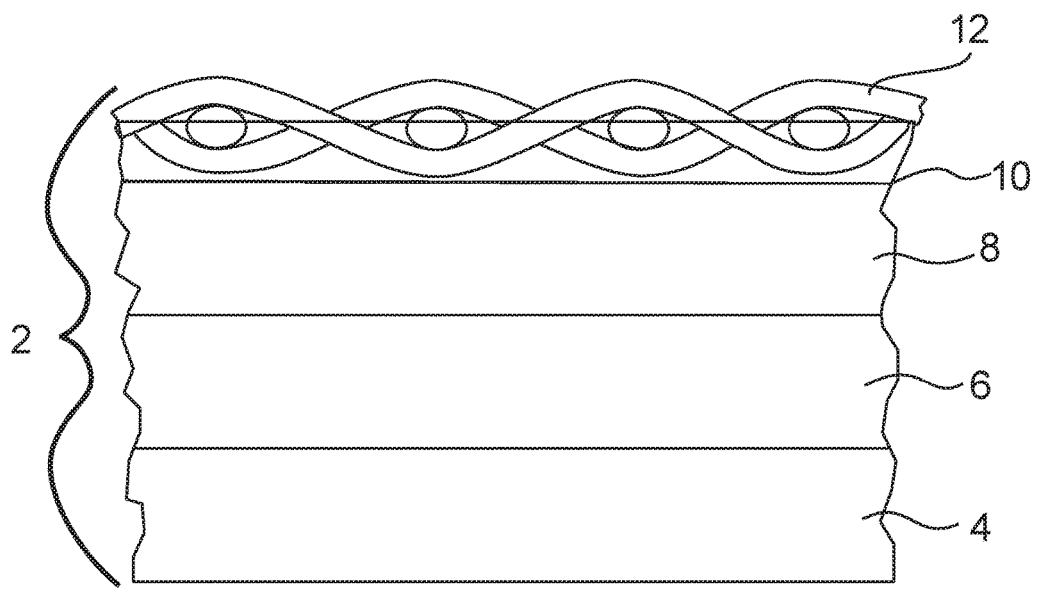
Figure 5A:
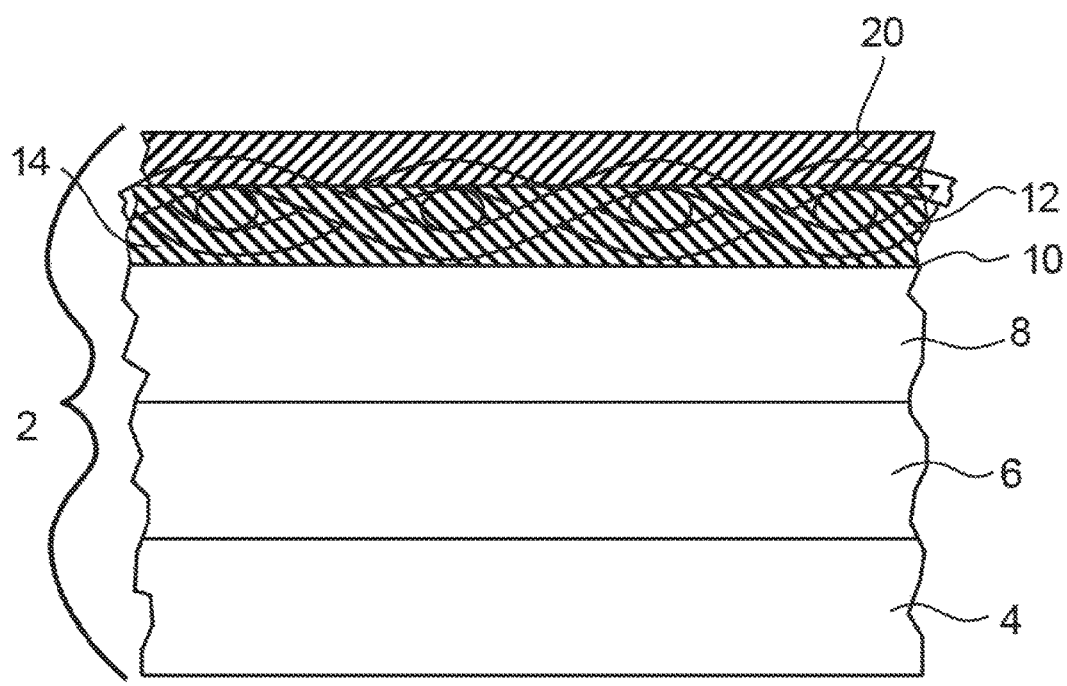
FIG. 5A shows a cross section of another embodiment of the present invention and FIG. 5B shows a cross section of a further embodiment of the present invention.

Alternative embodiments of FIGS. 1A and B is shown in FIGS. 5A and B. In addition to all the elements described in relation to the embodiment of FIGS. 1A and B, these embodiments have a further outer protective layer 20 over or incorporated into the outer surface of the substrate 12. This allows one to encapsulate the fibers of the substrate 12 making it more difficult to cause unraveling or pilling of the fibers of the substrate 12 and to further improve abrasion resistance of the resultant structure. Materials for such a layer can include polyethylene, polypropylene, nylons, ethylene vinyl acetate (EVA), EVA copolymers, styrene-butadiene polymers, copolymers and blends, polyesters, polyethylene teraphthalate (PET), thermoplastic elastomers (TPEs), polyurethanes the like.

Figure 5B:
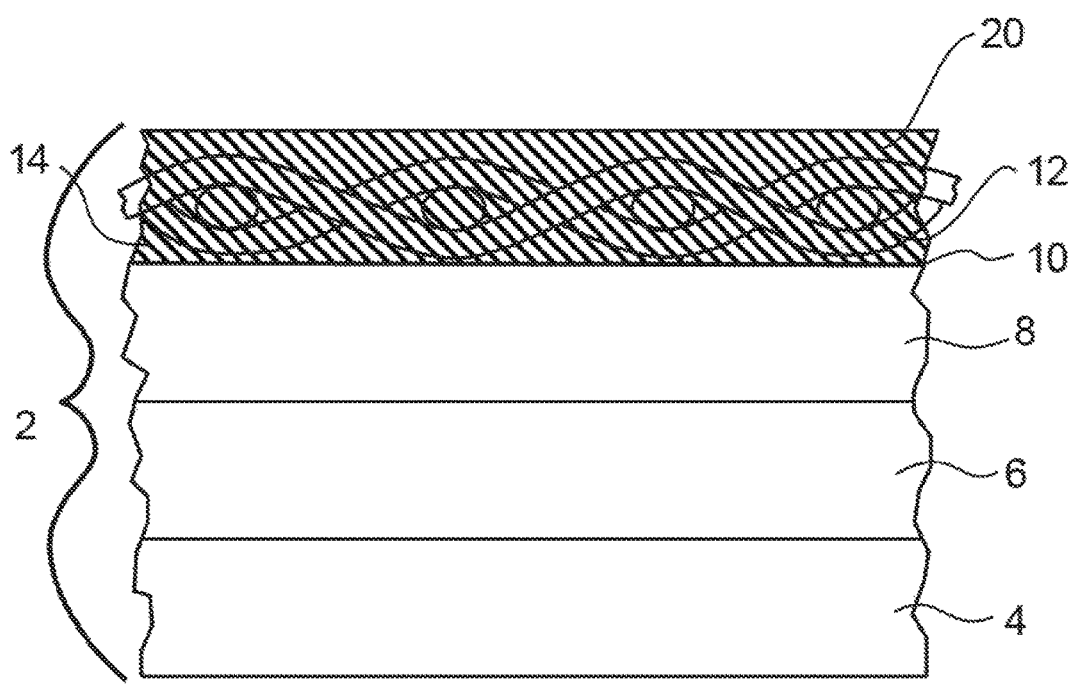

The outer protective layer 20 can be attached to the outer surface of the substrate 12 in the form of an additional resin layer such as a thermoplastic material or film which preferably is at least partially embedded into the substrate 12 as shown. The outer protective layer 20 may be provided with the substrate 12 or added to the substrate 12 before use. Alternatively, it can be formed as part of the film making process as an additional layer especially when a lamination process is used. In another embodiment, sufficient tie resin 14 is used when attaching the substrate 12 so as to enclose or envelope the thickness of the substrate 12 as shown in FIG. 5B.

In some instances, the outer protective layer 20 does not need a tie resin layer if the layer is partially incorporated into the outer surface of the substrate 12 as a heat bonded material or is integrated as part of the film manufacturing process such as a hot melt layer incorporated or extruded into a portion of the depth of the outer surface of the substrate 12 (FIG. 5A).

The substrate 12 can be formed of a clear or colored material. In some instances, it is desirable to have the substrate 12 formed of an opaque or light blocking material so that liquids which are sensitive to light, including UV and normal "white" light can be shielded by the substrate 12 to reduce or eliminate damage that would otherwise occur in a clear or transparent bag. Additives to block light, including UV light (additives such as titanium dioxide, zinc oxide and like or organic UV blockers are well known), can also be added to the substrate 12 or the coating or the tie resin layer 14, if used, or one or more layers of the film 2 as desired. Such light blocking additives are well known to one of skill in the art and are available from a variety of sources such as the Colormatrix™ Ultimate™ or the Colormatrix™ Lactra™ or the Oncap™ products from Polyone Corporation.

It is well known that film bags when inflated stretch under pressure. In some instances, inflation can cause the film 2 to stretch in unacceptable ways. For example, where a thinning of the film or other such defect occurs, the film portion that is thinner or has a defect may expand more rapidly than the rest of the film and create a bubble or other deformity in the film surface. This deformity can burst or be subject to greater/quicker wear under abrasion than the rest of the film and may lead to leaks. Likewise even where no thinning or other defect is in the film, an unconstrained film may inflate at different rates due to the way it was folded or unfolded or where it may have a crease or overlap or wrinkle in the film which can also lead to such bubbles or defects. Yet bags are often checked before use by a pressure test to ensure there are no pinholes or unsealed seams that may have been formed by a manufacturing error or by shipment and handling. This test is generally a pressure decay test in which the bag is inflated and then left for a period of time while the pressure and any decay of it is recorded.

However due to the bag's ability to stretch and create deformities, the pressure decay test needs to be done at a low pressure (typically under 1 and generally around 0.5 psi (3.5 KPa) and the bags are typically constrained such as by constraining the bag between two spaced apart restraining plates or being placed in a vacuum chamber or being placed into a holder of defined volume for that bag. Each of these techniques reduce or prevent the likelihood of a defect being formed on inflation. However due to the low pressure used the level of detection is corresponding low, meaning that only significantly large defects will be found (1000-2000 µm for bags ≥1000 L). Likewise, when using a walled chamber of spaced plates, some defects are covered or blinded and do not get detected. Lastly, as the pressure is low, the time involved in running such a test and determining whether a problem exists is extensive (5-10 minute test cycle). There is a need for a better, more accurate and quicker leak detection test before use.

With the present invention, one now has a bag that does not need to be mechanically constrained during a pressure decay test. Instead the outer substrate 12 itself constrains the film 2 and causes it to expand at an even rate thus reducing the potential for deformities, such as bubbles, being formed during the test. Additionally, the outer substrate 12 also allows one to use higher pressures (upwards of 3.5 to 15 psi (24-103 KPa)). This leads to more accurate and high levels of detection, making smaller defects, if they exist, detectable. Likewise, the use of a higher pressure allows for the test to be sped up significantly.

Figure 6:
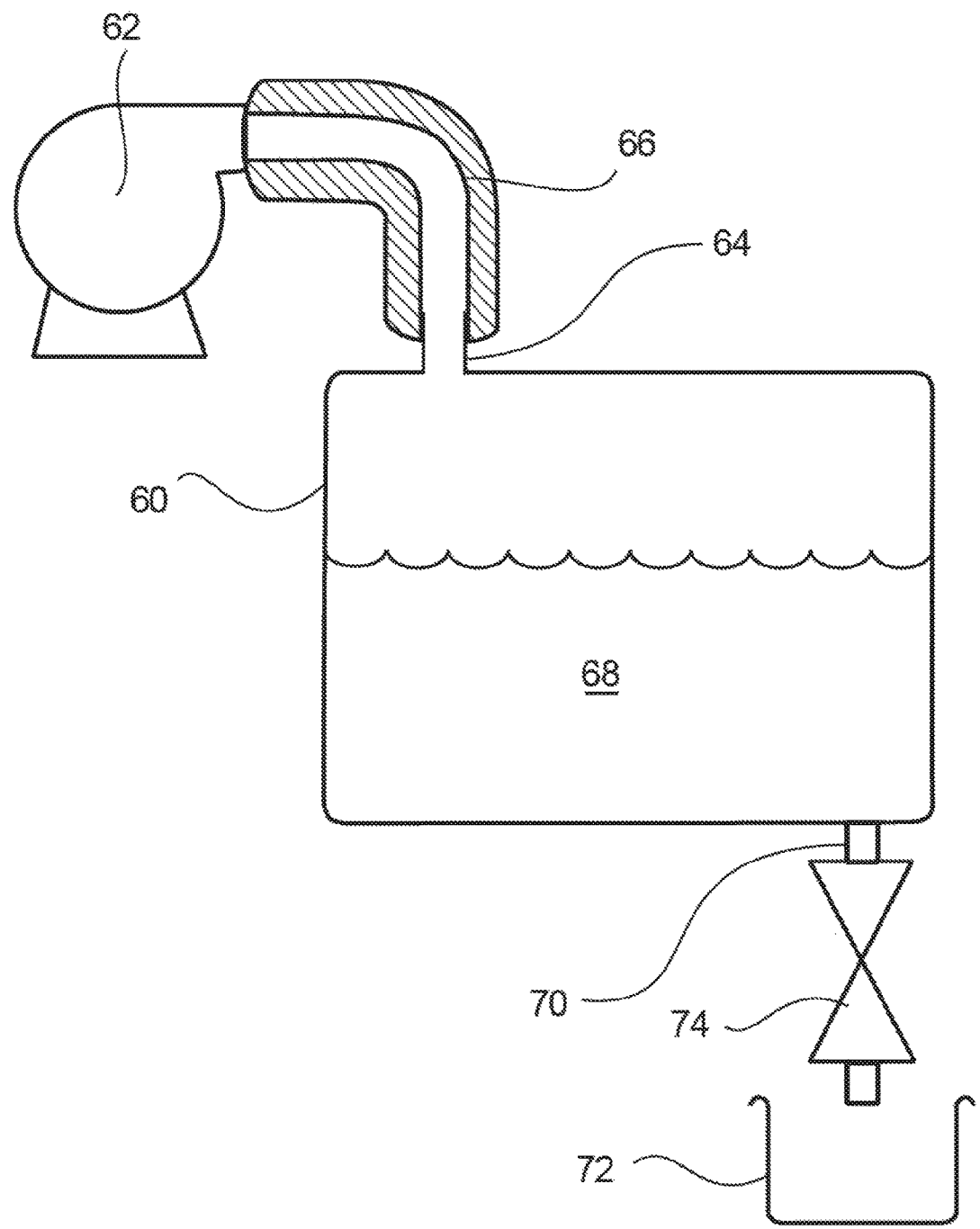
FIG. 6 shows a further embodiment of a biocontainer formed in accordance with the present invention in cross sectional view.

As shown in FIG. 6, a further advantage of the present invention is that the bag 60 can be self dispensing or self flowing, simply by using the air pressure within it to allow for the movement of liquid out of the bag. The bag 60 can have an air pressure system 62 such as an air pump or a supply of pressurized air attached to an inlet or port 64 via a tube or conduit 66. The bag 60 can be pressurized to a pressure of up to 15 psi (103 KPa) and this head pressure in the bag 60 can be used to cause the flow of liquid 68 within the bag 60 out an outlet or second port 70 when desired and as desired. As shown, the outlet 70 is located above a receiving vessel 72 or it may be connected to a another bag (not shown) via a tube or conduit or to a manifold containing a series of smaller bags (not shown) or to a dispensing head such as a valved needle (not shown) for dispensing the liquid 68 into vial or syringes. The outlet 70 may have a valve 74 or a clamp to selectively open and close the outlet as desired. The bag 60 may contain additional ports for pressure gauges and the like as well as one or more windows 30 as described above.

If desired, one can maintain the pressure within the bag 60 constant by supplying additional air pressure as the liquid is dispensed. This allows one to maintain the desired head pressure within the bag 60 so that the liquid can be fully dispensed at a constant rate from the bag 60. Alternatively, one can simply apply a fixed head pressure that reduces as liquid is dispensed from the bag 60.

In either embodiment, the use of valves, check valves, clamps, pressure gauges, windows and the like can also be used to maintain the system in its desired state and providing the desired dispensing or movement of liquid 68 out of the bag 60 as needed. All of these elements are well known to one of ordinary skill in the art.

Either embodiment eliminates the need for pumps to move liquid out of the bag 60. This can be of advantage in reducing system cost and complexity and in reducing the potential for shear damage to shear sensitive products that are dispensed from the bag 60 such as various protein solutions and the like.

Figure 7:
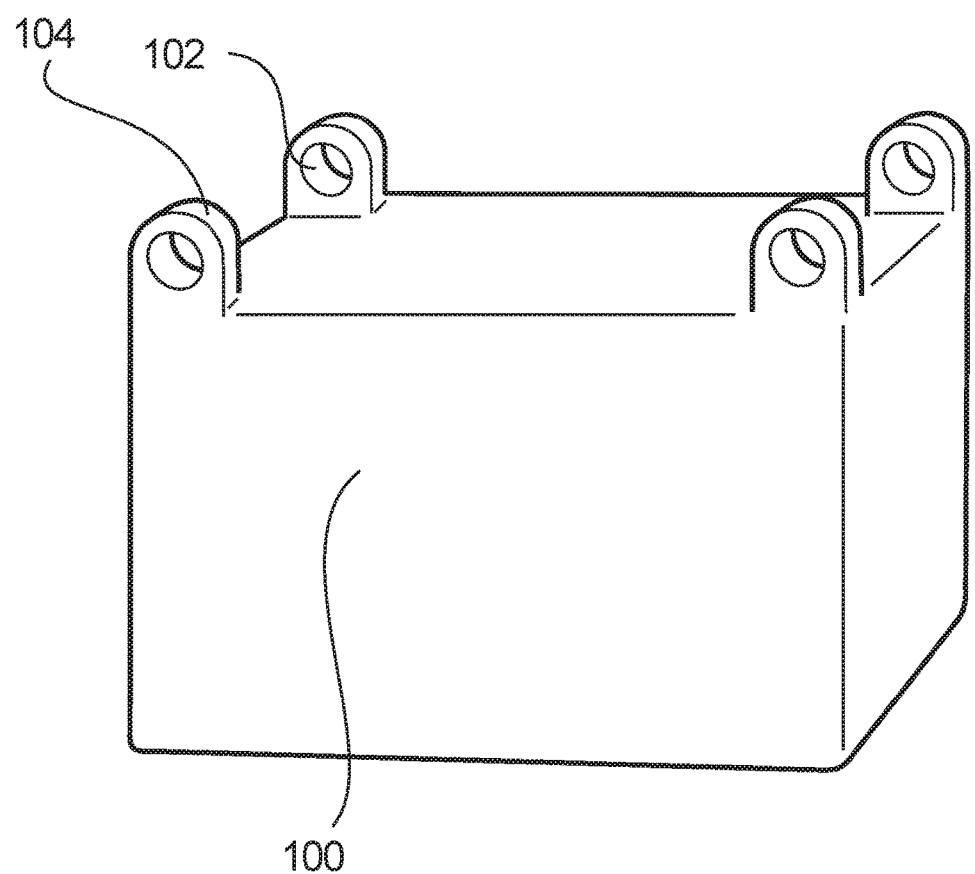
FIG. 7 shows a further embodiment of a biocontainer formed in accordance with the present invention in planar view.
Figure 8:
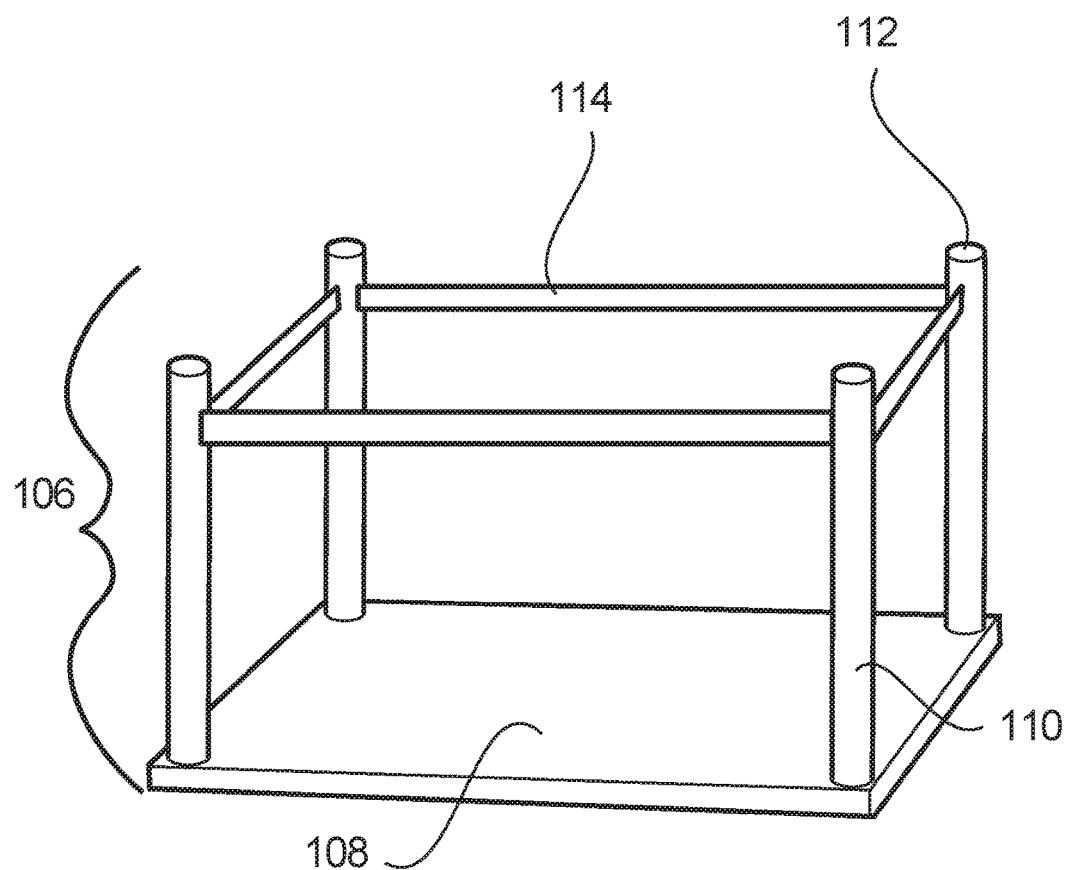
FIG. 8 shows an embodiment of a holder for the biocontainer formed in accordance with the present invention in planar view.

In a further embodiment of the present invention, the bag 100 may contain one or more grommets or eyes 102 especially at its upper corners 104 so that the bag 100 can be simply hang from a hook or preferably a carrier as shown in FIG. 7. As the substrate makes the bag 100 more resilient and self-supportive, there is less of a need for a rigid enclosed support vessel such as a vat or bin as is typically used with such containers. This allows one to use a simple framework 106 as shown in FIG. 8. As shown in FIG. 8, the framework 106 is formed of a base 108, and at least four vertically extending rods 110.

Preferably, and as shown, near the top ends 112 of each of the rods 110 are secondary substantially horizontal rods 114. Each secondary substantially horizontal rod 114 is connected to the adjacent rods 110 to complete the framework 106.

Figure 9:
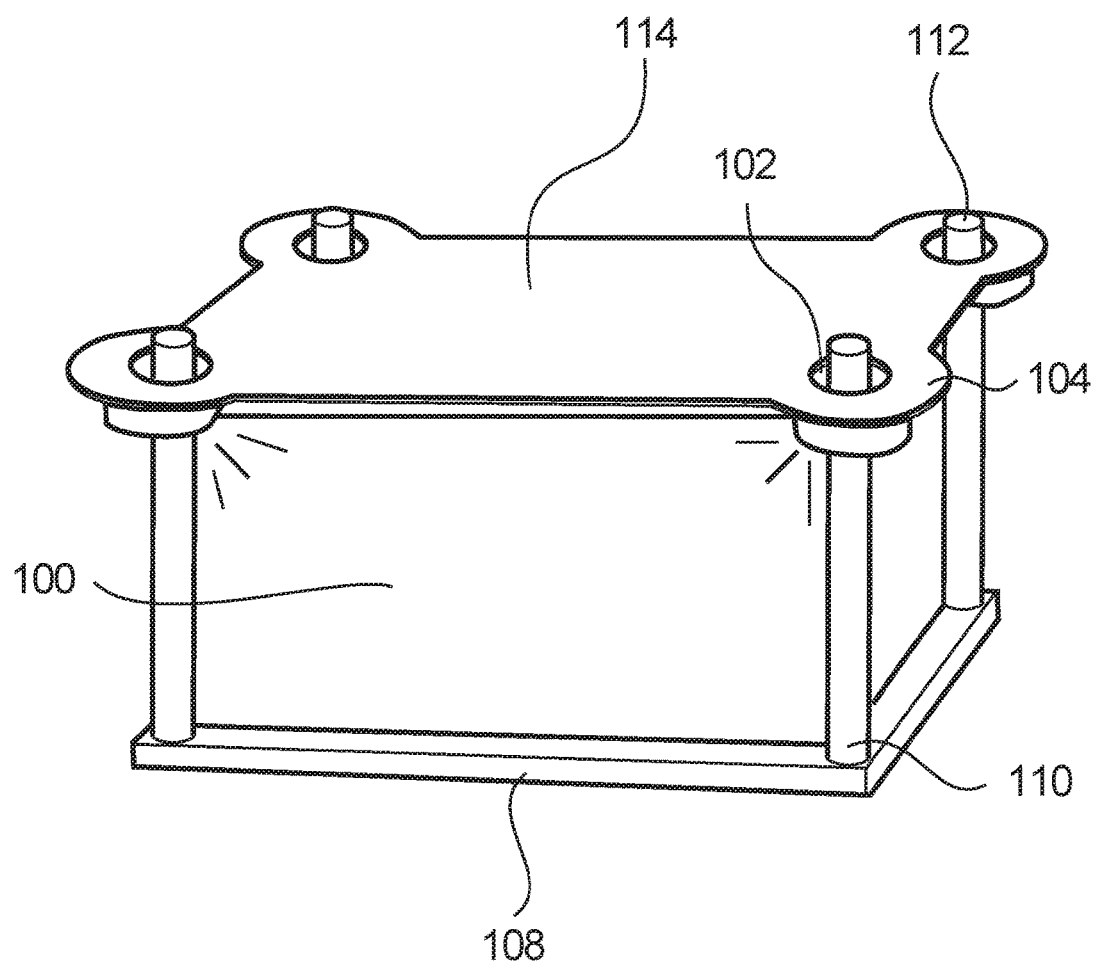
FIG. 9 shows the biocontainer of FIG. 7 mounted in the holder of FIG. 8 in planar view.

In either embodiment the grommets 102 are attached to the top ends 112 and the bag 100 is allowed to hang inside the framework 106 as shown in FIG. 9.

If desired additional secondary substantially horizontal rods 114 (not shown) can be located between the adjacent rods 110 at a location or locations further down toward the base 108 than the first set of rods 108. Alternatively, panels (not shown) may be used in lieu of or in conjunction with the secondary substantially horizontal rods 114.

EXAMPLES

Example 1

Three typical Single Use biocontainer films were compared to a composite substrate, made in according to the present invention, for abrasion and puncture resistance.

The substrate when used was extrusion coated onto the outer surface of the film using a polyethylene, copolymer attachment layer The attachment layer as embedded in the substrate was heated to a temperature of 500 degrees (F.)+/−20 degrees (F.) (260° C.+/−11° C.) and laminated under 10 pounds per square inch pressure by a roller.

A Taber Industries Linear Abrasion Tester was procured and a strip of each sample of 1.5 inch by 3 inch (3.8 cm×7.6 cm) was placed between the stylus and backing cylinder. Both the stylus and backing cylinder were capable of carrying an electrical current. The stylus was brought into contact with the surface of the sample or Control and reciprocated linearly over the surface of the material being tested with a stroke of 4 inches and at a cycle rate of 30 cycles per minute until an electrical connection between the stylus and backing cylinder is established (indicating loss of film integrity). The number of cycles each piece took to reach the loss of integrity was recorded. The number of cycles is an indication of the abrasion resistance of the material with the higher number of cycles indicating a more abrasion resistant material. The results are shown in Table 1 below.

Table 1 also indicates that standard puncture test was performed vis ASTM F1306. A pointed, metal tool is projected downward into a frame supported sample of the coated substrate.

TABLE 1

Abrasion & Puncture Testing of New Materials

| Material | Taber Abrasion[1] | Puncture[2] |
| --- | --- | --- |
| Nylon Woven/PE Film Composite | 2638 Cycles | 31.1 Lbs. |
| Unsupported Nylon/PE Film | 1100 Cycles | 11.2 Lbs. |
| Unsupported PET/PE Film | 984 Cycles | 16.4 Lbs. |
| Unsupported PE Film | 121 Cycles | 10.2 Lbs. |

[1]Taber Stylus Abrasion Test: 4 inch stroke length, 30 cycles per minute
[2]Per ASTM F1306 Puncture Test The results show that a substrate containing film has dramatically increased abrasion and puncture resistance compared to each of the non-laminated films.

Example 2

A biocontainer was formed using the substrate/film material according to the embodiment of Example 1. A window was formed in it by simply cutting out the window shape in the substrate before it was attached to the film.

Example 3

A first biocontainer was formed using a transparent substrate material (nylon woven fabric) which was laminated to the film material according to the embodiment of Example 1. A window formed in it by simply heating and compressing a window shape in the substrate before it was attached to the film. A second biocontainer was formed using a transparent substrate material (polyester nonwoven) which was laminated to the film material according to the embodiment of Example 1. A window formed in it by simply heating and compressing a window shape in the substrate before it was attached to the film.

Example 4

A biocontainer is formed using the substrate/film material according to the embodiment of Example 1. An outer protective layer is formed on the side of the substrate furthest from the film. A hot melt thermoplastic layer (polyethylene) is coated onto the substrate and compressed with a roller to cause the molten thermoplastic to penetrate into the substrate layer and form the outer protective layer.

Example 5

A control bag of 28"×20.5"×40" (71 cm×52 cm×101 cm) was made of Pureflex™ film (EMD Millipore) with a total of four panels for the top, bottom and sides. A polyethylene port having a hose barb extending from its sealing flange, with a through bore of 0.5 inch (1.27 cm) through the interior of the hose barb and flange, was heat sealed to the top panel of the bag to establish an opening between the bag interior and the port. A C-Flex® tube of 4 feet (121.92 cm) in length and having a 0.5 inch (1.27 cm) inside diameter was attached to the exterior of the hose barb and secured to it by a cable tie wrap. An Amesil pinch clamp was placed on the tube about 1 foot (30.48 cm) from the fitting. A bag according to the present invention was made using the same Pureflex™ film. The film had a nylon substrate (Sefar Medifab 03-300-51) secured to the outside surface of the film by extrusion coating. The bag had the same dimensions and same type of port, tubing and clamp located in the same position as the control bag. The clamps were removed from the tubes of each bag and both bags were inflated with air at 2 psi (0.138 bar) until they appeared to be fully inflated and taut. The clamps were then replaced on the tubes and the air was supply was disconnected. A pressure gauge (digital SSI Technologies MGI-200) was attached to the open end of end tube of each bag and the clamps were removed. The pressure was monitored for 15 minutes/hours for any pressure decay within each bag.

Example 6

A bag of 28"×20.5"×40" (71 cm×52 cm×101 cm) according to the present invention is made of Pureflex™ film (EMD Millipore). The film has a nylon substrate secured to the outside surface of the film by heat lamination. The biocontainer has a total of four panels for the top, bottom and sides. A first polyethylene inlet port having a hose barb extending from its sealing flange, with a through bore of 0.5 inch (1.27 cm) through the interior of the hose barb and flange, is heat sealed to the top panel of the biocontainer establishing the opening between the bag interior and the port. A second port of the same type and dimensions is attached to the bottom panel of the biocontainer. A silicone tube of 4 feet (121.92 cm) in length and having a 0.5 inch (1.27 cm) inside diameter is attached to the exterior of each hose barb and secured to each by a cable tie wrap. An Amesil pinch clamp is placed on each tube about 1 foot (30.48 cm) from each fitting. The clamps are removed and the top port is connected via the tube to an air pump capable of supplying air at 5 psi (0.345 bar) and the bottom port is connected to a container containing water via its tube. Water is added through the bottom port by removing the pinch clamp and pumping water into the biocontainer until the biocontainer was about 50% full. The bottom pinch clamp is closed and the upper pinch clamp removed. Air is supplied to the biocontainer until it reaches an internal pressure of 5 psi (0.345 bar). The bottom clamp is removed. The water is dispensed from the bag. Air pressure is intermittently supplied to the biocontainer when the pressure drops below 2 psi (0.138 bar). The water is dispensed without use of a pump.

What is claimed:

1. A material for biocontainers comprising:
   a multilayer film and a porous substrate attached to the multilayer film wherein the porous substrate is a woven nylon is embedded within the multilayer film or embedded within a tie resin layer, wherein the film comprises an outer strength zone formed of one or more polymeric layers disposed adjacent to the porous substrate,
   a gas impermeable zone disposed on the outer strength zone; the gas impermeable zone being made of ethylene vinyl alcohols; and
   a contact zone disposed on the outer strength zone, wherein the contact zone is formed of a low extractables polyolefin material, wherein an outer protective layer is formed on the substrate to encapsulate the substrate so as to provide abrasion resistance and puncture resistance.

2. The material of claim 1 wherein the substrate is formed with a polymer backing to attach the substrate to the film.

3. The material of claim 1 wherein the substrate is formed with a polymer backing to attach the substrate to the film, the substrate is formed of a material selected from the group consisting of woven and non-woven fibrous material and the polymer backing of the substrate is selected from the group consisting of polyolefins, polyurethanes and nylons.

4. The material of claim 1 wherein the substrate further comprises a material selected from the group consisting of woven fibrous material selected from the group consisting of polyester, aramids, carbon, metal and polyolefins.

5. The material of claim 1 wherein the substrate further comprises a non-woven fibrous material selected from the group consisting of nylon, polyester, aramids, carbon, metal and polyolefins.

6. A biocontainer having at least two walls and an inner volume defined by the at least two walls, the biocontainer being formed of the material of claim 1, wherein the contact zone is disposed on a surface of the inner volume.

7. The biocontainer of claim 6 wherein the substrate is formed of a material selected from the group consisting of woven and non-woven fibrous material and the polymer backing of the substrate is selected from the group consisting of polyolefins, polyurethanes and nylons.

8. The biocontainer of claim 6 wherein the substrate is formed of a material selected from the group consisting of woven fibrous material selected from the group consisting of nylon, polyester, aramids, carbon, metal and polyolefins.

9. The biocontainer of claim 6 wherein the substrate is formed of a non-woven fibrous material selected from the group consisting of nylon, polyester, aramids, carbon, metal and polyolefins.

10. The biocontainer of claim 6 wherein the film is formed of a multilayered film having a first interior zone, an intermediate gas impermeable zone and a support zone on the exterior side of the gas impermeable zone.

11. The biocontainer of claim 6 wherein the film is formed of a multilayered film having one or more layers of polyethylene and one or more layers of gas impermeable polymers.

12. The biocontainer of claim 6 wherein the film is formed of a multilayered film having a first interior side layer formed of one or more layers forming an inner contact zone, one or more layers of a gas impermeable zone and one or more layers of polymers on the exterior side of the of gas impermeable zone forming an outer strength zone.

13. The biocontainer of claim 6 wherein the substrate has one or more openings formed in it to provide a device selected from the group consisting of a viewing port and a port.

14. The biocontainer of claim 6 wherein the substrate has one or more elongate openings formed in it to provide a viewing port into the interior of the biocontainer.

15. A method of testing a biocontainer of claim 6 comprising attaching a gas pressure source to an inlet of the biocontainer, closing any other inlet or outlet in the biocontainer, attaching a pressure gauge to the biocontainer or pressure source to read the pressure within the biocontainer, inflating the biocontainer until full and at a desired pressure and monitoring the pressure over time to determine whether any pressure decay occurs.

16. The material of claim 1 wherein the substrate has one or more openings formed in it to provide a device selected from the group consisting of a viewing port and a port.

17. A method of dispensing comprising a biocontainer having at least two walls and an inner volume defined by the at least two walls, the biocontainer being formed of a material having an inner film and an outer porous substrate attached to each other wherein the outer porous substrate is formed of a woven fibrous nylon material so as to provide abrasion resistance to the biocontainer, the biocontainer being filled with a desired volume of a liquid, attaching a pressure source with a pressure gauge to the biocontainer, attaching a valve to the outlet of the biocontainer, inflating the biocontainer to a desired pressure and selectively opening and closing the valve to dispense the liquid, wherein the porous woven fibrous nylon material is embedded within the inner film or embedded within a tie resin layer, wherein the inner film comprises an outer strength zone formed of one or more polymeric layers disposed adjacent to the porous substrate, a gas impermeable zone disposed on the outer strength zone; the gas impermeable zone being made of ethylene vinyl alcohols; and a contact zone disposed on the outer strength zone, wherein the contact zone is formed of a low extractables polyolefin material, wherein an outer protective layer is formed on the porous substrate to encapsulate the porous substrate so as to provide abrasion resistance and puncture resistance.

18. The method of claim 17 wherein the biocontainer is pressurized once.

19. The method of claim 17 further comprising adding additional gas pressure to the biocontainer when it reaches a threshold minimum pressure during dispensing.

* * * * *